United States Patent
Marshall et al.

(10) Patent No.: US 6,380,259 B2
(45) Date of Patent: Apr. 30, 2002

(54) USE OF SUBSTITUTED AMIDINO COMPOUNDS IN THE TREATMENT OF CHRONIC OBSTRUCTIVE PULMONARY DISEASE

(75) Inventors: Paul J. Marshall, Flanders; Roger A. Fujimoto, Morristown, both of NJ (US)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 09/732,453

(22) Filed: Dec. 7, 2000

Related U.S. Application Data

(63) Continuation of application No. 09/435,943, filed on Nov. 9, 1999, which is a continuation of application No. 09/210,634, filed on Dec. 11, 1998, now abandoned, which is a continuation of application No. 08/989,367, filed on Dec. 12, 1997, now abandoned.
(60) Provisional application No. 60/112,002, filed on Dec. 12, 1997.

(51) Int. Cl.$^7$ ............................................. A61K 31/165
(52) U.S. Cl. ...................... 514/617; 514/618; 514/620; 514/621; 514/622
(58) Field of Search ................................ 514/617, 618, 514/620, 621, 622

(56) References Cited

U.S. PATENT DOCUMENTS

| | | | |
|---|---|---|---|
| 5,246,965 A | 9/1993 | Main | 514/532 |
| 5,451,700 A | * 9/1995 | Morrissey et al. | 564/165 |
| 5,455,274 A | * 10/1995 | Suh | 514/620 |
| 5,488,160 A | * 1/1996 | Morrissey | 564/165 |
| 5,639,768 A | 6/1997 | Morrissey et al. | 514/353 |
| 5,686,496 A | 11/1997 | Anderskewitz et al. | 514/637 |
| 5,846,963 A | * 12/1998 | Arabeo et al. | 514/178 |

FOREIGN PATENT DOCUMENTS

| | | |
|---|---|---|
| WO | 9316036 | 8/1993 |
| WO | 9411341 | 5/1994 |
| WO | 9421616 | 9/1994 |
| WO | 9602496 | 2/1996 |
| WO | 9602497 | 2/1996 |
| WO | 9721670 | 6/1997 |

OTHER PUBLICATIONS

Fujimoto et al. "The Preclinical and Clinical Pharmacology of CGS 25019C, an Orally Active LTB4 Receptor Antagonist," 10$^{th}$ International Conference on Prostaglandins and Related Compounds, Sep. 22–27, 1996.
DE 4424713—Abstract Only.
J.S. Sawyer—Leukotriene B4 Receptor Antagonists: Recent Clinical Developments—Expert Opinion on Investigational Drugs, vol. 5, No. 1, 1996, pp. 73–77, XP002101783.
Cohen et al.—Recent Progress in the Development of Leukotriene B4 Antagonists—Curr. Opin. Invest. Drugs, vol. 3, No. 1, 1994, pp. 13–22, XP002101784.
Seggev, et al., Serum Leukotriene B4 Levels in Patients with Obstructive Pulmonary Disease—Chest—vol. 99, No. 2, 1989, pp. 289–291, XP002101785.

* cited by examiner

Primary Examiner—James H. Reamer
(74) Attorney, Agent, or Firm—Carol A. Loeschorn

(57) ABSTRACT

Use in medicaments for the treatment of chronic obstructive pulmonary disease of compounds of formula

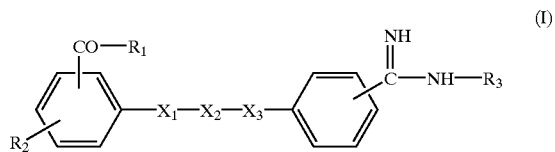

(I)

wherein the C(=NH)—NHR$_3$ group may be in tautomeric or isomeric form, or a pharmaceutically acceptable salt thereof, in which:

R$_1$ is amino which is mono- or disubstituted by a substituent selected from an aliphatic hydrocarbon radical, an araliphatic hydrocarbon radical, an aromatic radical, and a cycloaliphatic hydrocarbon radical or is amino which is disubstituted by a divalent aliphatic hydrocarbon radical or a said radical interrupted by oxygen;

R$_2$ is hydrogen, halogen, trifluoromethyl, an aliphatic hydrocarbon radical, hydroxy or is hydroxy which is etherified by an aliphatic, araliphatic or aromatic alcohol or by an aliphatic alcohol which is substituted by carboxy, by esterified carboxy or by amidated carboxy or which is esterified by an aliphatic or araliphatic carboxylic acid;

R$_3$ is hydrogen or an acyl radical which is derived from an organic carbonic acid, an organic carboxylic acid, a sulfonic acid, or a carbamic acid;

X$_1$ and X$_3$, independently or one another, are oxygen (—O—) or sulphur (—S—); and X$_2$ is a divalent aliphatic hydrocarbon radical which may be interrupted by an aromatic radical;

wherein the phenyl rings of formula I may be, independently or one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid;

wherein aryl in the above definitions may be, independently of one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid;

wherein a cycloaliphatic hydrocarbon radical may be substituted by an aliphatic radical.

21 Claims, No Drawings

USE OF SUBSTITUTED AMIDINO COMPOUNDS IN THE TREATMENT OF CHRONIC OBSTRUCTIVE PULMONARY DISEASE

This is a continuation of U.S. patent application Ser. No. 09/435,943 filed Nov. 9, 1999, pending, which is a continuation of U.S. patent application Ser. No. 09/210,634, filed Dec. 11, 1998, abandoned, which is a continuation of U.S. Patent Application No. 60/112,002, filed Dec. 12, 1997, which is a continuation of U.S. patent application No. Ser. 08/989,367, filed Dec. 12, 1997, now abandoned.

This invention relates to the use of organic compounds, particularly substituted amidino compounds, in the treatment of chronic obstructive respiratory diseases, particularly chronic obstructive pulmonary disease (COPD), including emphysema, cystic fibrosis and, especially, chronic bronchitis.

COPD is one of the major causes of death and disability in the USA and Europe and there are no effective therapies currently available which prevent progression of the disease. The most common causal mechanism is cigarette smoking, which leads to chronic bronchitis. About 15% of smokers develop progressive airflow limitation, which is largely due to emphysema.

The invention provides, in one aspect, the use, for the preparation of a medicament for the treatment of chronic obstructive pulmonary disease, of a pharmacologically active compound of formula

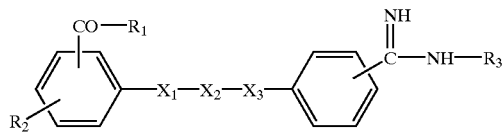

wherein the C(=NH)—NHR$_3$ group may be in tautomeric or isomeric form, or a pharmaceutically acceptable salt thereof, in which:

R$_1$ is amino which is mono- or disubstituted by a substituent selected from an aliphatic hydrocarbon radical, an araliphatic hydrocarbon radical, an aromatic radical, and a cycloaliphatic hydrocarbon radical or is amino which is disubstituted by a divalent aliphatic hydrocarbon radical or a said radical interrupted by oxygen;

R$_2$ is hydrogen, halogen, trifluoromethyl, an aliphatic hydrocarbon radical, hydroxy or is hydroxy which is etherified by an aliphatic, araliphatic or aromatic alcohol or by an aliphatic alcohol which is substituted by carboxy, by esterified carboxy or by amidated carboxy or which is esterified by an aliphatic or araliphatic carboxylic acid;

R$_3$ is hydrogen or an acyl radical which is derived from an organic carbonic acid, an organic carboxylic acid, a sulfonic acid, or a carbamic acid;

X$_1$ and X$_3$, independently of one another, are oxygen (—O—) or sulphur (—S—); and X$_2$ is a divalent aliphatic hydrocarbon radical which may be interrupted by an aromatic radical;

wherein the phenyl rings of formula I may be, independently of one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid;

wherein aryl in the above definitions may be, independently of one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid;

wherein a cycloaliphatic hydrocarbon radical may be substituted by an aliphatic radical.

In another aspect, the invention provides pharmacologically active compounds of formula I and pharmaceutically acceptable salts thereof for use in the treatment of chronic obstructive pulmonary disease.

In a further aspect, the invention provides a method for the treatment of chronic obstructive pulmonary disease which comprises administering to a mammal in need of such treatment an effective amount of a pharmacologically active compound of formula I, or a pharmaceutically acceptable salt thereof, as hereinbefore defined.

The compounds of formula I wherein the C(=NH)—NHR$_3$ group is in tautomeric or isomeric form are represented by formula I$^1$

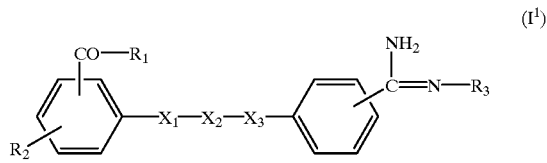

wherein R$_1$, R$_2$, R$_3$, X$_1$, X$_2$ and X$_3$ have the meanings as defined for formula I.

As compounds of formula I have a basic centre, they can thus form acid addition salts, especially pharmaceutically acceptable salts. These are formed, for example, with inorganic acids, such as mineral acids, for example sulfuric acid, a phosphoric or hydrohalic acid, or with organic carboxylic acids, such as (C$_1$–C$_4$)-alkanecarboxylic acids which, for example, are unsubstituted or substituted by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, benzoic acid or with organic sulfonic acids, such as (C$_1$–C$_4$)-alkane- or arylsulfonic acids which are unsubstituted or substituted, for example, by halogen, for example methane- or toluenesulfonic acid. Preferred are salts formed with hydrochloric acid, methanesulfonic acid and maleic acid, especially maleic acid.

The general definitions used below have, if not defined differently, the following meanings:

An aliphatic hydrocarbon radical is, for example, lower alkyl, lower alkenyl and secondarily lower alkynyl.

An araliphatic hydrocarbon radical is, for example, optionally substituted phenyl-lower alkyl and secondarily phenyl-lower alkenyl and phenyl-lower alkynyl.

A cycloaliphatic hydrocarbon radical is, for example, cycloalkyl and secondarily cycloalkenyl, which is unsubstituted or mono- or polysubstituted, for example, disubstituted, by lower alkyl.

A divalent aliphatic hydrocarbon radical is, for example, lower alkylene.

A divalent aliphatic radical interrupted by oxygen is, for example, lower alkylene interrupted by oxygen, e.g. ethylene-O-ethylene.

A divalent aliphatic hydrocarbon radical which is interrupted by an aromatic radical is, for example, lower alkylene-phenylene-lower alkylene or lower alkylene-naphthylene-lower alkylene.

An aliphatic alcohol is, for example, a lower alkanol or lower alkenol, and an araliphatic alcohol is, for example, a phenyl-lower alkanol, for example benzyl alcohol.

Hydroxy which is etherified by an aliphatic or araliphatic alcohol is, for example, lower alkoxy or lower alkenyloxy and phenyl-lower alkoxy.

Hydroxy etherified by an aliphatic alcohol substituted by carboxy, esterified carboxy or amidated carboxy is, for example, lower alkoxy substituted by carboxy, by lower alkoxycarbonyl, by aryl-lower alkoxycarbonyl, by aminocarbonyl or by mono- or di-lower alkylaminocarbonyl.

An aliphatic carboxylic acid is, for example, a lower alkanoic or lower alkenoic acid, and an araliphatic carboxylic acid is, for example, a phenyl-lower alkanoic acid.

Hydroxy which is esterified by an aliphatic or araliphatic carboxylic acid is, for example, lower alkanoyloxy, lower alkenoyloxy or phenyl-lower alkanoyloxy.

An acyl radical which is derived from an organic carboxylic acid is, for example, lower alkanoyl, phenyl-lower alkanoyl or unsubstituted or substituted aroyl, such as benzoyl, naphthoyl, indanoyl or fluorenoyl, or heteroaroyl such as pyridylcarbonyl, thienylcarbonyl, pyrrolylcarbonyl, furanylcarbonyl and imidazolylcarbonyl.

An acyl radical which is derived form an organic carbonic acid is, for example, alkoxycarbonyl or alkenyloxycarbonyl which in each case are unsubstituted or substituted by an aromatic radical or is cycloalkoxycarbonyl which unsubstituted or substituted by lower alkyl.

An acyl radical which is derived from a sulfonic acid is, for example, alkanesulfonyl, arylalkanesulfonyl, cycloalkanesulfonyl or arylsulfonyl.

An acyl radical which is derived from a carbamic acid is, for example, amino-carbonyl which is substituted by alkyl, arylalkyl or aryl.

An aromatic radical is, for example, unsubstituted or substituted such as monosubstituted or polysubstituted, for example, disubstituted or secondarily trisubstituted carbocyclic aryl, such as phenyl, naphthyl, indanyl or fluorenyl, or heterocyclic aryl, such as pyridyl, thienyl, pyrrolyl, furanyl, and imidazolyl.

Aryl represents preferably monocarbocyclic aryl, advantageously optionally substituted phenyl, such being phenyl or phenyl substituted by e.g. lower alkyl, lower alkoxy, halogen or trifluoromethyl.

The phenyl rings of formulae I and $I^1$ as well as aromatic radicals referred to before and hereafter are generally unsubstituted or further substituted such as monosubstituted or polysubstituted, for example disubstituted or secondarily trisubstituted, in particular, for example, by a substituent selected from the group consisting of halogen, trifluoromethyl, lower alkyl, lower alkenyl, lower alkynyl, hydroxy, lower alkoxy, lower alkenyloxy, phenyl-lower alkoxy, lower alkanoyloxy, lower alkenoyloxy, and phenyl-lower alkanoyloxy. Preferably, the phenyl rings of formula I and $I^1$ do not exhibit any additional substitutent.

Preferred positions of the following structural elements in the corresponding phenyl ring in formula I are: positions 4 (para) or 5 (meta) for —C—$R_1$, position 2 (ortho) or 3 (meta) for $R_2$, and position 4 (para) for —C(=NH)—$NHR_3$ grouping and both tautomeric and isomeric forms are encompassed by the instant invention.

The term "substituted by one or more substituents" refers preferably to one, two or three such substituents, advantageously one or two.

The expression "lower" means that corresponding groups and compounds in each case contain in particular not more than 7, preferably not more than 4, carbon atoms.

Halogen is, in particular, fluorine, chlorine or bromine, and furthermore includes iodine.

Lower alkyl is, in particular, $C_1$–$C_7$-alkyl and is, for example, methyl, ethyl, n-propyl, isopropyl, n-butyl, isobutyl, sec-butyl, tert-butyl and furthermore includes corresponding pentyl, hexyl and heptyl radicals. $C_1$–$C_4$-alkyl is preferred.

Lower alkenyl is, in particular, $C_3$–$C_7$-alkenyl and is, for example, 2-propenyl or 1-, 2- or 3-butenyl. $C_3$–$C_5$-Alkenyl is preferred.

Lower alkynyl is, in particular, $C_3$–$C_7$-alkynyl and is preferably propargyl.

Phenyl-lower alkyl is, in particular, phenyl-$C_1$–$C_4$-alkyl and is preferably benzyl, 1- and 2-phenethyl, while phenyl-lower alkenyl and phenyl-lower alkynyl are, in particular, phenyl-$C_2$–$C_5$alkenyl and -alkynyl, in particular 2-phenyl-vinyl, 3-phenylallyl and 3-phenylpropargyl.

Cycloalkyl is, in particular, $C_3$–$C_7$-cycloalkyl and is, for example, cyclopropyl, cyclobutyl, cyclopentyl, cyclohexyl and cycloheptyl. Cyclopentyl and cyclohexyl are preferred.

Cycloalkenyl is, in particular, $C_3$–$C_7$-cycloalkenyl and is preferably cyclopent-2- or -3-enyl, or cyclohex-2- and -3-en-yl.

Lower alkylene e.g. in amino which is disubstituted by lower alkylene is, in particular, $C_2$–$C_6$-alkylene and is, for example, butylene, pentylene, or 2,6-hexylene. Preferred is $C_4$–$C_5$-alkylene, especially pentylene.

Lower alkylene $X_2$ is, in particular, $C_2$–$C_8$-alkylene, preferably straight-chain, and is, for example, ethylene, propylene, butylene, pentylene, hexylene, heptylene and also octylene. $C_4$–$C_7$-Alkylene is preferred, especially pentylene and also butylene, hexylene or heptylene.

Lower alkylene which is interrupted by a phenyl radical ($X_2$) is, in particular, lower alkylene-phenylene-lower alkylene or lower alkylene-napthylene-lower alkylene such as $C_2$–$C_4$-alkylene-phenylene-$C_2$–$C_4$-alkylene or $C_2$–$C_4$-alkylene-napthylene-$C_2$–$C_4$-alkylene, preferably straight-chain, and is, for example, methylene-phenylene-methylene, 1,2-ethylene-phenylene-1,2-ethylene, such as 1,2-ethylene-1,4-phenylene-1,2-ethylene, 1,3-propylene-phenylene-1,3-propylene, such as 1,3-propylene-1,4-phenylene-1,3-propylene, or butylene-phenylene-butylene radicals, also a corresponding 1,2-ethylene-napthylene-1,2-ethylene radical.

$C_2$–$C_4$-alkylene-phenylene-$C_2$–$C_4$-alkylene or $C_2$–$C_3$-alkylene-napthylene-$C_2$–$C_3$-alkylene is preferred, especially 1,2-ethylene-1,4-phenylene- 1,2-ethylene.

Lower alkoxy is, in particular, $C_1$–$C_7$-alkoxy and is, for example, methoxy, ethoxy, n-propyloxy, isopropyloxy, n-butyloxy, isobutyloxy, sec-butyloxy, tert-butyloxy and furthermore includes corresponding pentyloxy, hexyloxy and heptyloxy radicals. $C_1$–$C_4$-Alkoxy is preferred.

Lower alkenyloxy is, in particular, $C_3$–$C_7$-alkenyloxy and is, for example, allyloxy or but-2-en- or but-3-enyloxy. $C_3$–$C_5$-Alkenyloxy is preferred.

Phenyl-lower alkoxy is, in particular, phenyl-$C_1$–$C_4$-alkoxy, such as benzyloxy, 1- or 2-phenylethoxy, or 1-, 2- or 3-phenylpropyloxy.

Lower alkanoyloxy is, in particular, $C_2$–$C_8$-alkanoyloxy, in particular, $C_2$–$C_5$-alkanoyloxy, such as acetyloxy, propionyloxy or pivaloyloxy.

Lower alkenoyloxy is, in particular, $C_3$–$C_8$-alkenoyloxy, in particular, $C_3$–$C_5$-alkenoyloxy, such as propenoyloxy.

Phenyl-lower alkanoyloxy is, in particular, phenyl-$C_2$–$C_8$-alkanoyloxy, in particular, phenyl-$C_2$–$C_5$- alkanoyloxy, such as phenylacetyloxy, phenylpropionloxy or phenylpivaloyloxy.

Alkoxycarbonyl is, in particular, $C_2-C_{12}$-alkoxycarbonyl and is, for example, methoxy-, ethoxy-, propyloxy-pivaloxy or oxtyloxy-carbonyl. $C_2-C_9$-Alkoxycarbonyl is preferred.

Alkenyloxycarbonyl is, in particular, $C_3-C_{12}$-alkenyloxycarbonyl, for example, allyloxycarbonyl. Preferred is $C_3-C_5$-alkenyloxycarbonyl.

Cycloalkyloxycarbonyl is, in particular, $C_3-C_7$-cycloalkyloxycarbonyl, preferred is cyclopentyloxycarbonyl or cyclohexyloxycarbonyl.

Alkanesulfonyl is, in particular, $C_1-C_7$alkanesulfonyl and is, for example, methane-, ethane-, n-propane- or isopropanesulfonyl. $C_1-C_4$-Alkanesulfonyl is preferred.

Arylalkanesulfonyl is, in particular, phenyl-$C_1-C_7$alkanesulfonyl, for example, benzyl- or 1- and 2-phenylethan-sulfonyl. Phenyl-$C_1-C_4$-alkane-sulfonyl is preferred.

Cycloalkanesulfonyl is, in particular, $C_3-C_7$-cycloalkanesulfonyl, preferred is cyclopentanesulfonyl or cyclohexanesulfonyl.

Naphthyl is 1- or 2-naphthyl.

Indanyl is, for example, 1-, 2-, 3- or 4-indanyl.

Fluorenyl is, for example, 1-, 2-, 3-, 4- or 5-fluorenyl.

Lower alkanoyl is, in particular, $C_1-C_7$-alkanoyl and is, for example, formyl, acetyl, propionyl, butyryl, isobutyryl or pivavolyl. $C_2-C_5$-Alkanoyl is preferred.

Phenyl-lower alkanoyl is, in particular, phenyl-$C_2-C_7$-alkanoyl and is, for example, phenylacetyl or 2- or 3-phenylpropionyl. Phenyl-$C_2-C_4$-alkanoyl is preferred.

Substituted aroyl represents aroyl, such as benzoyl, which is substituted e.g. by lower alkoxy, lower alkyl, hydroxy, hydroxymethyl or by acyloxymethyl (such as lower alkanoyloxymethyl or benzoyloxymethyl.

Naphthoyl is 1- or 2-naphthoyl.

Indanoyl is, for example, 1-, 2-, 3- or 4-indanoyl.

Fluorenoyl is, for example, 1-, 2-, 3- 4- or 5-fluorenoyl.

Esterified carboxyl represents preferably lower alkoxycarbonyl or aryl-lower alkoxycarbonyl.

Amidated carboxyl represents preferably aminocarbonyl, mono- or di-lower alkylaminocarbonyl, (mono-aryl-mono-lower alkyl)aminocarbonyl, mono- or di-(aryl-lower alkyl) aminocarbonyl or (mono-aryl-lower alkyl-mono-lower alkyl)aminocarbonyl.

The invention relates preferably to the use of compounds of formula I and pharmaceutically acceptable salts thereof, in which:

$R_1$ is amino which is mono- or disubstituted by a substituent selected from lower alkyl, lower alkenyl, lower alkynyl, phenyl-lower alkyl, phenyl-lower alkenyl, phenyl-lower alkynyl, phenyl, napthyl, indanyl, fluorenyl, cycloalkyl, and cycloalkenyl, cycloalkyl and cycloalkenyl each being unsubstituted or mono- or polysubstituted by lower alkyl, or is amino which is disubstituted by lower alkylene;

$R_2$ is hydrogen, halogen, trifluoromethyl, lower alkyl, lower alkenyl, lower alkynyl, hydroxy, lower alkoxy, lower alkenyloxy, phenyl-lower alkoxy, phenoxy, lower alkoxy substituted by carboxy, lower alkoxycarbonyl, aminocarbonyl or mono- or di-lower alkylaminocarbonyl, lower alkanoyloxy, lower alkenoyloxy or phenyl-lower alkanyloxy;

$R_3$ is hydrogen, alkoxycarbonyl or alkenyloxycarbonyl, each of which is unsubstituted or substituted by phenyl, naphthyl, indanyl or fluorenyl, or is cycloalkoxycarbonyl being unsubstituted or mono- or polysubstituted by lower alkyl, or is lower alkanoyl or phenyl-lower alkanoyl, or is benzoyl, naphthoyl, indanoyl or fluorenoyl, or is $C_1-C_7$-alkanesulfonyl, phenyl-$C_1-C_7$alkanesulfonyl, $C_3-C_7$-cycloalkanesulfonyl, or phenylsulfonyl, or is aminocarbonyl which is substituted by lower alkyl, phenyl-lower alkyl or phenyl;

$X_1$ and $X_3$, independently of one another, are O or S;

$X_1$ is lower alkylene, lower alkylene-phenylene-lower alkylene or lower alkylene-naphthylene-lower alkylene;

wherein the phenyl rings of formula I may be, independently of one another, substituted by one or more substituents selected from halogen, trifluoromethyl, lower alkyl, lower alkenyl, lower alkynyl, hydroxy, lower alkoxy, lower alkenyloxy, phenyl-lower alkoxy, lower alkanoyloxy, lower alkenoyloxy and phenyl-lower alkanoyloxy;

wherein the aromatic radicals in the above definitions may be, independently of one another, substituted by one or more substituents selected from halogen, trifluoromethyl, lower alkyl, lower alkenyl, lower alkynyl, hydroxy, lower alkoxy, lower alkenyloxy, phenyl-lower alkoxy, lower alkanoyloxy, lower alkenoyloxy and phenyl-lower alkanoyloxy.

The invention especially relates to the use of compounds of formula I and pharmaceutically acceptable salts thereof, in which:

$R_1$ is amino which is mono- or disubstituted by a substituent selected from $C_1-C_7$-alkyl, phenyl-$C_1-C_7$-alkyl, phenyl and $C_3-C_6$-cycloalkyl, $C_3-C_6$-cycloalkyl being unsubstituted or mono- or polysubstituted by $C_1-C_7$alkyl, or is amino which is disubstituted by $C_3-C_6$-alkylene;

$R_2$ is hydrogen, hydroxy, $C_1-C_7$-alkoxy, $C_1-C_7$-alkoxy substituted by carboxy or lower alkoxycarbonyl or phenyl-$C_1-C_4$ alkoxy;

$R_3$ is hydrogen, $C_1-C_{12}$-alkoxy-carbonyl, $C_2-C_5$-alkanoyl, phenyl-$C_2-C_5$-alkanoyl, benzoyl which is unsubstituted or substituted by halogen, trifluoromethyl, $C_1-C_7$-alkyl, or $C_1-C_7$ alkoxy, $C_3-C_6$-cycloalkylcarbonyl which is unsubstituted or substituted by $C_1-C_7$-alkyl, or is benzoyl, naphthoyl, indanoyl or fluorenoyl, or is $C_1-C_7$alkanesulfonyl, phenyl-$C_1-C_7$alkanesulfonyl, $C_3-C_7$-cycloalkanesulfonyl, or phenylsulfonyl, or is aminocarbonyl which is substituted by $C_1-C_7$-alkyl, phenyl-$C_1-C_7$-alkyl or phenyl;

$X_1$ and $X_3$ each are —O—, or furthermore are, independently of one another, —O— or —S—;

$X_2$ is $C_2-C_7$-alkylene or $C_2-C_4$-alkylene-phenylene-$C_2-C_4$-alkylene;

wherein the phenyl rings of formula I may be unsubstituted or, furthermore, independently of one another, substituted by one or more substituents selected from halogen, trifluoromethyl, $C_1-C_7$-alkyl, and $C_1-C_7$-alkoxy;

wherein phenyl in the above definitions is unsubstituted or, furthermore, independently of one another, substituted by one or more substituents selected from halogen, trifluoromethyl, $C_1-C_7$-alkyl, and $C_1-C_7$-alkoxy.

The invention especially relates to the use of compounds of formula I and pharmaceutically acceptable salts thereof, in which —CO—$R_1$ is located in position 4 (para) or 3 or 5 (meta) of the corresponding phenyl ring with respect to -$X_1$-; $R_2$- is located in position 2 (ortho) or 3 (meta) of the corresponding phenyl ring with respect to -X$_1$-; and —C(=NH)—NHR$_3$ is located in position 4 (para) of the corresponding phenyl ring with respect to -X$_3$-.

The invention especially relates to the use of compounds of formula IA

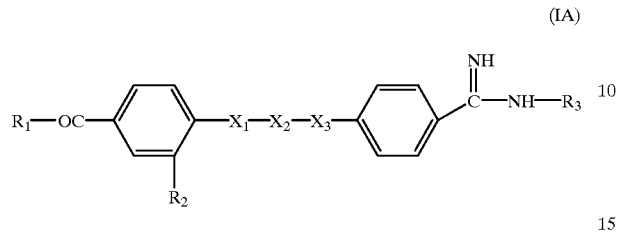

(IA)

wherein the C(=NH)—NHR$_3$ group may be in tautomeric or isomeric form, and pharmaceutically acceptable salts thereof, in which:

R$_1$ is di-C$_1$–C$_4$-alkylamino, such as di-ethylamino or di-isopropylamino, C$_1$–C$_4$alkyl-(phenyl)amino, such as phenyl-isopropyl-amino, C$_1$–C$_4$alkyl-(phenyl-C$_1$–C$_4$-alkyl)-amino, such as methyl-benzyl-amino, di-C$_3$–C$_6$-cycloalkylamino, such as di-cyclohexylamino, which is unsubstituted or substituted by C$_1$–C$_4$-alkyl, or 1-piperidino substituted by C$_1$–C$_4$-alkyl, such as 2-methyl-1-piperidino;

R$_2$ is hydrogen, C$_1$–C$_4$-alkoxy such as methoxy or C$_1$–C$_4$-alkoxy which is substituted by carboxy, lower alkoxycarbonyl, aminocarbonyl or by mono- or di-lower alkylaminocarbonyl;

R$_3$ is hydrogen, C$_1$–C$_{12}$-alkoxycarbonyl, such as methoxycarbonyl or octyloxycarbonyl, phenyl-C$_1$–C$_4$-alkoxycarbonyl, such as benzyloxycarbonyl, C$_2$–C$_5$-alkanoyl, such as acetyl, benzoyl which is unsubstituted or substituted by halogen, trifluoromethyl, C$_1$–C$_4$-alkyl or by C$_1$–C$_4$-alkoxy, such as 3,4-dimethoxybenzoyl, C$_3$–C$_6$-cycloalkylcarbonyl which is unsubstituted or substituted by C$_1$–C$_4$-alkyl, such as 2-isopropyl-5-methyl-cyclohexylcarbonyl;

X$_1$ and X$_3$ are —O—;

X$_2$ is C$_4$–C$_7$-alkylene, such as pentylene;

wherein the phenyl rings of formula IA may be unsubstituted or, furthermore, independently of one another, substituted by one or more substituents selected from halogen, trifluoromethyl, C$_1$–C$_4$-alkyl, and C$_1$–C$_4$-alkoxy.

The invention especially relates to the use of compounds of formula IA and pharmaceutically acceptable salts thereof, in which:

R$_1$ is di-C$_1$–C$_4$-alkylamino, such as di-ethylamino or di-isopropylamino, C$_1$–C$_4$-alkyl-(phenyl)-amino, such as phenyl-isopropyl-amino, C$_1$–C$_4$-alkyl-(phenyl-C$_1$–C$_4$-alkyl)-amino, such as methyl-benzyl-amino, di-C$_3$–C$_6$-cycloalkylamino, such as di-cyclohexylamino which is unsubstituted or substituted by C$_1$–C$_4$-alkyl, or 1-piperidino substituted by C$_1$–C$_4$-alkyl, such as 2-methyl-1-piperidino;

R$_2$ is hydrogen, C$_1$–C$_4$-alkoxy such as methoxy or C$_1$–C$_4$-alkoxy which is substituted by carboxy, lower alkoxycarbonyl, aminocarbonyl or mono- or di-lower alkylaminocarbonyl;

R$_3$ is C$_1$–C$_4$alkanesulfonyl, such as methane-, ethane- or isopropanesulfonyl, phenyl-C$_1$–C$_4$-alkanesulfonyl, such as benzylsulfonyl, C$_3$–C$_7$-cycloalkane-sulfonyl, such as cyclohexanesulfonyl, or phenylsulfonyl, or is aminocarbonyl which is substituted by C$_1$–C$_4$-alkyl, phenyl-C$_1$–C$_4$-alkyl or phenyl;

X$_1$ and X$_3$ are —O—;

X$_2$ is C$_4$–C$_7$-alkylene, such as pentylene.

The invention especially relates to the use of compounds of formula IA and pharmaceutically acceptable salts thereof, in which:

R$_1$ is di-C$_1$–C$_4$-alkylamino, such as di-ethylamino or di-isopropylamino, C$_1$–C$_4$-alkyl-(phenyl)-amino, such as phenyl-isopropyl-amino, C$_1$–C$_4$-alkyl-(phenyl-C$_1$–C$_4$-alkyl)-amino, such as methyl-benzyl-amino, di-C$_3$–C$_6$-cycloalkylamino, such as di-cyclohexylamino which is unsubstituted or substituted by C$_1$–C$_4$-alkyl, or 1-piperidino substituted by C$_1$–C$_4$-alkyl, such as 2-methyl-1-piperidino;

R$_2$ is hydrogen, C$_1$–C$_4$-alkoxy such as methoxy or C$_1$–C$_4$-alkoxy substituted by C$_1$–C$_4$-alkoxycarbonyl, such as ethoxycarbonylmethyl, or by aminocarbonyl;

R$_3$ is hydrogen; or R$_3$ is lower alkanoyl, such as acetyl;

X$_1$ and X$_3$ are —O—;

X$_2$ is C$_4$–C$_7$-alkylene, such as pentylene.

The invention further especially relates to the use of compounds of formula IA and pharmaceutically acceptable salts thereof, in which;

R$_1$ is di-C$_1$–C$_4$-alkylamino, such as di-isopropylamino;

R$_2$ is hydrogen, C$_1$–C$_4$-alkoxy such as methoxy or C$_1$–C$_4$-alkoxy substituted by C$_1$–C$_4$-alkoxycarbonyl or by aminocarbonyl R$_3$ is C$_1$–C$_{12}$-alkoxycarbonyl, such as methoxycarbonyl or octyloxycarbonyl, phenyl-C$_1$–C$_4$-alkoxycarbonyl, such as benzyloxycarbonyl, C$_2$–C$_5$-alkanoyl, such as acetyl, benzoyl which is unsubstituted or substituted by halogen, trifluoromethyl, C$_1$–C$_4$-alkyl, or C$_1$–C$_4$-alkoxy, such as 3,4-dimethoxybenzoyl, C$_3$–C$_6$-cycloalkylcarbonyl which is unsubstituted or substituted by C$_1$–C$_4$-alkyl, such as 2-isopropyl-5-methyl-cyclohexylcarbonyl;

X$_1$ and X$_3$ are —O—;

X$_2$ is C$_4$–C$_7$-alkylene, especially pentylene.

The invention further especially relates to the use of compounds of formula IA and pharmaceutically acceptable salts thereof, in which:

R$_1$ is di-C$_1$–C$_4$-alkylamino, such as di-ethylamino or di-isopropylamino;

R$_2$ is hydrogen, C$_1$–C$_4$-alkoxy such as methoxy or C$_1$–C$_4$-alkoxy substituted by C$_f$–C$_4$-alkoxycarbonyl such as ethoxycarbonyl or by aminocarbonyl, R$_3$ is hydrogen or C$_1$–C$_4$-alkanoyl, such as acetyl;

X$_1$ and X$_3$ are —O—;

X$_2$ is C$_4$–C$_7$-alkylene, especially pentylene.

The invention also particularly relates to the use of compounds of formula IB

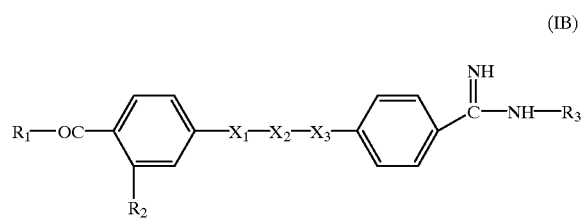

(IB)

wherein the C(=NH)—NHR$_3$ group may be in tautomeric or isomeric form, and pharmaceutically acceptable salts thereof, in which:

$R_1$ is di-$C_1$–$C_4$-alkylamino, such as di-ethylamino or di-isopropylamino, $C_1$–$C_4$alkyl-(phenyl)amino, such as phenyl-isopropyl-amino, $C_1$–$C_4$-alkyl-(phenyl-$C_1$–$C_4$-alkyl)-amino, such as methyl-benzyl-amino, di-$C_3$–$C_6$-cycloalkylamino, such as di-cyclohexylamino, which is unsubstituted or substituted by $C_1$–$C_4$-alkyl, or 1-piperidino substituted by $C_1$–$C_4$-alkyl, such as 2-methyl-1-piperidino;

$R_2$ is hydroxy or $C_1$–$C_4$-alkoxy which is substituted by carboxy, lower alkoxycarbonyl, aminocarbonyl or by mono- or di-lower alkylaminocarbonyl;

$R_3$ is hydrogen, $C_1$–$C_{12}$-alkoxycarbonyl, such as methoxycarbonyl or octyloxycarbonyl, phenyl-$C_1$–$C_4$-alkoxycarbonyl, such as benzyloxycarbonyl, $C_2$–$C_5$-alkanoyl, such as acetyl, benzoyl which is unsubstituted or substituted by halogen, trifluoromethyl, $C_1$–$C_4$-alkyl, or $C_1$–$C_4$-alkoxy, such as 3,4-dimethoxybenzoyl, $C_3$–$C_6$-cycloalkylcarbonyl which is unsubstituted or substituted by $C_1$–$C_4$-alkyl, such as 2-isopropyl-5-methyl-cyclohexylcarbonyl;

$X_1$ and $X_3$ are —O—;

$X_2$ is $C_4$–$C_7$-alkylene, such as pentylene;

wherein the phenyl rings of formula IB may be unsubstituted or, furthermore, independently of one another, substituted by one or more substituents selected from halogen, trifluoromethyl, $C_1$–$C_4$-alkyl, and $C_1$–$C_4$-alkoxy.

The invention especially relates to the use of compounds of formula IB and pharmaceutically acceptable salts thereof, in which:

$R_1$ is di-$C_1$–$C_4$-alkylamino, such as di-ethylamino or di-isopropylamino, $C_1$–$C_4$-alkyl-(phenyl)-amino, such as phenyl-isopropyl-amino, $C_1$–$C_4$-alkyl-(phenyl-$C_1$–$C_4$-alkyl)-amino, such as methyl-benzyl-amino, di-$C_3$–$C_6$-cycloalkylamino, such as di-cyclohexylamino, which is unsubstituted or substituted by $C_1$–$C_4$-alkyl, or 1-piperidino substituted by $C_1$–$C_4$-alkyl, such as 2-methyl-1-piperidino;

$R_2$ is hydroxy or $C_1$–$C_4$-alkoxy which is substituted by carboxy, lower alkoxycarbonyl, aminocarbonyl or mono- or di-lower alkylaminocarbonyl;

$R_3$ is $C_1$–$C_4$alkanesulfonyl, such as methane-, ethane- or isopropanesulfonyl, phenyl-$C_1$–$C_4$-alkanesulfonyl, such as benzylsulfonyl, $C_3$–$C_7$-cycloalkane-sulfonyl, such as cyclohexanesulfonyl, or phenylsulfonyl, or is aminocarbonyl which is substituted by $C_1$–$C_4$-alkyl, phenyl-$C_1$–$C_4$-alkyl or phenyl;

$X_1$ and $X_3$ are —O—;

$X_2$ is $C_4$–$C_7$-alkylene, such as pentylene.

The invention especially relates to the use of compounds of formula IB and pharmaceutically acceptable salts thereof, in which:

$R_1$ is di-$C_1$–$C_4$-alkylamino, such as di-ethylamino or di-isopropylamino, $C_1$–$C_4$-alkyl-(phenyl)-amino, such as phenyl-isopropyl-amino, $C_1$–$C_4$alkyl-(phenyl-$C_1$–$C_4$-alkyl)-amino, such as methyl-benzyl-amino, di-$C_3$–$C_6$-cycloalkylamino, such as di-cyclohexylamino, which is unsubstituted or substituted by $C_1$–$C_4$-alkyl, or 1-piperidino substituted by $C_1$–$C_4$-alkyl, such as 2-methyl-1-piperidino;

$R_2$ is hydroxy or $C_1$–$C_4$-alkoxy substituted by $C_1$–$C_4$-alkoxycarbonyl, such as ethoxycarbonylmethoxy or by aminocarbonyl, such as carbamoylmethoxy;

$R_3$ is hydrogen; or $R_3$ is $C_2$–$C_5$-alkanoyl, such as acetyl;

$X_1$ and $X_3$ are —O—;

$X_2$ is $C_4$–$C_7$-alkylene, such as pentylene.

The invention further especially relates to the use of compounds of formula IB and pharmaceutically acceptable salts thereof, in which:

$R_1$ is di-$C_1$–$C_4$-alkylamino, such as di-ethylamino or di-isopropylamino;

$R_2$ is hydroxy or $C_1$–$C_4$-alkoxycarbonylmethoxy, such as ethoxycarbonylmethoxy, or aminocarbonylmethoxy;

$R_3$ is hydrogen or $C_2$–$C_5$-alkanoyl, such as acetyl;

$X_1$ and $X_3$ are —O—;

$X_2$ is $C_4$–$C_7$-alkylene, especially pentylene.

Specific especially preferred compounds are those described in WO 94/11341, EP 0518819, U.S. Pat. Nos. 5,451,700 and 5,488,160, particularly the Examples of those publications.

The invention relates particularly to the use of a compound of formula IA and pharmaceutically acceptable salts thereof in which $R_1$ is di-isopropylamino, $R_2$ is methoxy, $R_3$ is hydrogen, $X_1$ and $X_3$ are —O— and $X_2$ is pentylene and a compound of formula IB and pharmaceutically acceptable salts thereof in which $R_1$ is di-isopropylamino, $R_2$ is hydroxy, $R_3$ is hydrogen, $X_1$ and $X_3$ are —O— and $X_2$ is pentylene, especially the maleate salts of said compounds.

Compounds of formula I and their salts where $R_2$ is hydroxy etherified by an aliphatic alcohol which is substituted by carboxy, esterified carboxy or amidated carboxy and their preparation are described in WO 94/11341. Other compounds of formula I and their salts and their preparation are described in EP 0518819, U.S. Pat. Nos. 5,451,700 and 5,488,160.

Compounds of formula IB may also be prepared by catalytic hydrogenation of a compound of formula

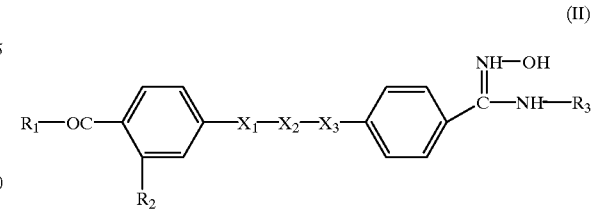

(II)

where $R_1$, $R_2$, $R_3$, $X_1$, $X_2$ and $X_3$ are as defined in formula IB, to reduce the indicated hydroxyimino group to imino, for example using palladium-carbon as the catalyst in a mixture of ethanol and acetic acid when the compound of formula IB is isolated as the acetate salt which may be converted if desired into other salts such as the maleate salt or into the free amidine using known procedures.

Compounds of formula II may be prepared as described in U.S. Pat. No. 5,455,274.

The maleate (2-butenedioate) salt of the compound of formula IB in which $R_1$ is di-isopropylamino, $R_2$ is hydroxy, $R_3$ is hydrogen, $X_1$ and $X_3$ are —O— and $X_2$ is pentylene is novel per se. This salt, 4-[5-[4-(aminoiminomethyl)phenoxy]pentoxy]-2-hydroxy-N,N-bis(1-methylethyl)benzamide (Z)-2-butenedioate may be prepared as described in the Example hereinafter.

The compounds of formula I may be prepared in the form of one of the possible isomers or mixtures thereof, for example, as substantially pure geometric (cis or trans) isomers, optical isomers (antipodes), racemates, or mixtures thereof.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. Racemic amidines (wherein $R_3$ represents hydrogen) can thus be resolved into their optical antipodes e.g. by fractional crystallization of a salt formed with an optically active acid.

In view of the close relationship between the free compounds and the compounds in the form of their salts, whenever a compound is referred to in this context, a corresponding salt is also intended, provided such is possible or appropriate under the circumstances.

The compounds, including their salts, can also be used in the form of their hydrates, or include other solvents used for their crystallization.

The compounds of formula I and their salts can be administered enterally, such as orally or rectally, by the pulmonary route, e.g. by inhalation, transdermally and parenterally to mammals, including man, in an effective amount alone or in combination with one or more pharmaceutically acceptable carriers.

The active compound may be administered in a composition containing, for example, from about 0.1% to about 95%, such as from about 1% to about 80%, from about 10% to about 80% or, preferably from about 20% to about 60%, of the active compound. Examples of pharmaceutical compositions for enteral or parenteral administration are those in dose-unit forms such as coated tablets, tablets, capsules or suppositories, as well as ampoules. These are prepared in a manner known per se, for example using conventional mixing, granulating, coating, dissolving or freeze-drying processes. Thus, pharmaceutical products for oral use can be obtained by combining the active compound with solid excipients, where appropriate granulating a mixture which is obtained, and processing the mixture or granules, if desired or necessary, after addition of suitable auxiliaries to tablets or cores of coated tablets.

Preferred compositions for enteral or parenteral administration are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. Cores of coated tablets are provided with suitable, optionally enteric, coatings, using, inter alia, concentrated sugar solutions which optionally contain gum arabic, talc, polyvinylpyrrolidone, polyethylene glycol and/or titanium dioxide, lacquer solutions in suitable organic solvents or solvent mixtures or, for the preparation of enteric coatings, solutions of suitable cellulose products such as acetyl cellulose phthalate or hydroxypropylmethylcellulose phthalate. Colorants or pigments can be added to the tablets or coatings of coated tablets, for example, to identify or to indicate various doses of active compound. In addition, they may also contain other therapeutically valuable substances. Said compositions are prepared according to conventional mixing, granulating or coating methods, respectively, and contain about 0.1 to 75%, preferably about 1 to 50%, of the active ingredient.

A medicament, i.e. a pharmaceutical composition, suitable for pulmonary administration may comprise a compound of formula I or a pharmaceutically acceptable salt thereof, as hereinbefore defined, optionally in admixture with a pharmaceutically acceptable carrier therefor, the compound or mixture being in inhalable form. For example, the medicament may be in the form of an aerosol, which can be prepared in accordance with well-known procedures, or in finely divided particulate form comprising, for example, the active ingredient in finely divided form together with a carrier such as finely divided lactose. Such medicaments may be administered using an inhaler device suitable for the inhalable form, such devices being well-known in the art.

An aerosol composition suitable for use in the method of the invention may comprise a compound of formula I or a pharmaceutically acceptable salt thereof in solution, or dispersed, in a propellant, which may be chosen from any of the propellants known in the art, such as fluorocarbons. The concentration of the active ingredient in the propellant may be up to about 5% by weight, for example 0.1 to 5%, 0.1 to 3%, 0.1 to 2%, 0.2 to 2%, 0.5% to 2% or 1 to 2% by weight.

An inhalable medicament in finely divided particulate form may comprise a compound of formula I or pharmaceutically acceptable salt thereof alone or together with a finely divided solid carrier such as glucose, lactose, mannitol, sorbitol, ribose, mannose, arabinose, saccharose, galactose, fructose or xylose. In such a medicament, the compound of formula I or salt thereof suitably has a median particle size of up to 10 microns, preferably up to 5 microns, especially up to 3 microns. Suitably, at least 70%, preferably at least 80%, of the particles present in such a particulate medicament have a median particle size of up to 10 microns, preferably up to 5 microns, especially up to 3 microns.

In accordance with the foregoing, the invention also provides a pharmaceutical composition comprising as active ingredient a compound of formula I, or a pharmaceutically acceptable salt thereof, as hereinbefore defined, for use in the treatment of chronic obstructive pulmonary disease.

In conjunction with another active ingredient, a compound of formula I or a pharmaceutically acceptable salt thereof may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 70 kg may contain e.g. between about 1 and about 1000 mg/kg per day of the active ingredient.

The effect of compounds of formula I or their pharmaceutically acceptable salts in the treatment of chronic obstructive pulmonary disease can be tested in a murine model of pulmonary neutrophilia induced by lipopolysaccharide via intranasal instillation. Bacterial lipopolysaccharide (LPS) is a macromolecular cell surface antigen of bacteria which, when applied in vivo triggers a network of inflammatory responses. The main characteristics of this LPS-induced lung inflammation model, macrophage activation, tumour necrosis factor -α (TNF-α) production and neutrophil infiltration and activation, are features of chronic obstructive pulmonary disease. This model causes pulmonary inflammation as an acute injury which occurs after 2 to 4 hours in the airway lumen, where all the inflammatory parameters can be assessed by bronchoalveolar lavage (BAL).

The compound under test is dissolved in dimethyl sulfoxide (DMSO) and to the resulting solution is added sterile phosphate buffered saline (PBS) (50 μl). The final concentration of DMSO is 2%. Female Balb/C mice (20–25 g) are treated intranasally, under Halothane/oxygen/nitrous oxide anaesthesia, with the PBS DMSO diluent containing the compound under test at a suitable dose (0.1–30 mg/kg) or with diluent alone and, 30 minutes later, with 0.3 mg/kg of LPS (Salmonella Typhosa, Sigma). The animals are housed in plastic cages in an air conditioned room at 24° C. Food and water are available ad libitum. 3 hours after intranasal administration of LPS, terminal anaesthesia is induced with pentobarbitone sodium (60 mg/kg, i.p.), the abdominal cavity is opened and the animals are exsanguinated by withdrawal of blood from a major blood vessel.

The trachea is cannulated and bronchoalveolar lavage (BAL) is performed by injecting 4 times 0.3 ml of PBS into the lung via the trachea. The fluid is then immediately withdrawn and the cell suspension stored on ice. Total cell count is measured and cytospin preparation (Shandon Scientific Ltd, Cheshire, UK) prepared. Cells are stained with Dif-Quick (Baxter Dade AG, Dudingen, Switzerland) and a differential count of 200 cells performed using standard morphological criteria. The remaining lavage fluids are centrifuged at 1200 rpm for 10 minutes, the supernatant is aliquoted and stored at −80° C.

BAL myeloperoxidase (MPO) activity is measured on fresh BAL supernatant using a 96 well plate format colorometric assay. 50 μl of the samples, in duplicate, are mixed with 100 μl of the substrate buffer for 5 minutes at room temperature (sodium phosphate 50 mM, pH 6.0 containing 0.5% hexadecyltrimethylammonium bromide, 0.167 nM o-dianisidine dihydrochloride and 0.4 mM $H_2O_2$). The reaction is stopped with 100 μl of 5% sodium azide in distilled water and the optical density (OD) read at 450 nm. Results are expressed as U/ml using a standard curve established with human leukocyte myeloperoxidase (Sigma).

The inhibitory effect of the compound under test on lung inflammation is shown by the reduced neutrophil count and/or reduced MPO activity obtained after administration of the compound compared with that obtained after administration of diluent alone.

In a modification of the above procedure, the compound under test (or diluent alone for comparative purposes) is intranasally administered a second time at the same dosage, 6 hours after administration of LPS and the terminal anaesthesia is carried out 18 hours after the second administration. Another modification of the above procedure which can be used is described by Goncalves de Moraes et al, 1996 British Journal of Pharmacology, 117, 1792–1796.

EXAMPLE

4-[5-[4-(amino(hydroxyimino)methyl)phenoxy]pentoxy]-2-hydroxy-N,N-bis(1-methylethyl)benzamide prepared as described in U.S. Pat. No. 5,455,274 (100.76 g), 370 mL of acetic acid, and 800 mL of ethanol are gently shaken and warmed to 50–52° C. to form a slightly yellow solution. 10% palladium-carbon (13.2 g) is added and the mixture is hydrogenated at 60 psi at a temperature 52–54° C. for 24 hours. The hot reaction mixture is filtered through a celite and the filter cake is washed twice with 75 mL of 2:1 ethanol/acetic acid. The solvents are then removed in vacuo at 75° C. Toluene (200 mL) is added to the residue and the solvents are evaporated in vacuo. This is repeated a second time to remove trace amounts of acetic acid and ethanol. To the residue is added 10 g of activated charcoal and 50 mL of 2-propanol, and the mixture is heated to 75° C. The slurry is filtered hot and washed twice with 50 mL of 2-propanol. 4-[5-[4-(aminoiminomethyl)phenoxy]pentoxy]- 2-hydroxy-N,N-bis(1-methylethyl)benzamide monoacetate is crystallized from 2-propanol as the product, m.p. 197–199° C.

| CHN calculated for $C_{27}H_{38}N_3O_6$ | | | |
|---|---|---|---|
| Theory: | %C: 64.78 | %H: 7.65 | %N: 8.40 |
| Found: | %C: 64.80 | %H: 8.10 | %N: 8.13 |

4-[5-[4-(aminoiminomethyl)phenoxy]pentoxy]-2-hydroxy-N,N-bis(1-methylethyl)benzamide monoacetate (75.24 g) is suspended in 550 mL of anhydrous ethanol (550 mL) and stirred under a nitrogen atmosphere and heated to 75° C. A solution of 34.82 g of maleic acid in 75 mL of water is heated to 75° C. and rapidly added to the mixture. Then 7 g of activated carbon is added, and the black slurry is heated to 80° C. and filtered through a celite layer. The filter-cake is washed with ethanol/water (85 ml/15 mL), and cooled overnight to room temperature. The reaction mixture is cooled to 3~5° C. for 2 hours and 4-[5-[4-(aminoiminomethyl)phenoxy]pentoxy]-2-hydroxy-N,N-bis(1-methylethyl)benzamide (Z)-2-butenedioate (1:1) is collected as white crystals, m.p. 212° C.

| CHN calculated for $C_{29}H_{39}N_3O_8$ | | | |
|---|---|---|---|
| Theory: | %C: 62.46 | %H: 7.05 | %N: 7.54 |
| Found: | %C: 62.20 | %H: 6.92 | %N: 7.38 |

What is claimed is:

1. A method for the treatment of chronic obstructive pulmonary disease which comprises administering to a mammal in need of such treatment an effective amount of a pharmacologically active compound of formula

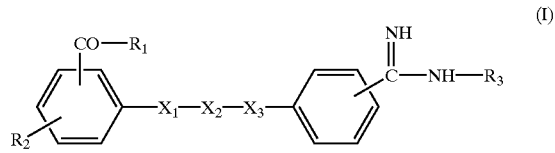

(I)

wherein the C(=NH)—NHR$_3$ group may be in tautomeric or isomeric form; or a pharmaceutically acceptable salt thereof, in which:

$R_1$ is amino which is mono- or disubstituted by a substituent selected from an aliphatic hydrocarbon radical, an araliphatic hydrocarbon radical, an aromatic radical, and a cycloaliphatic hydrocarbon radical or is amino which is disubstituted by a divalent aliphatic hydrocarbon radical or a said radical interrupted by oxygen;

R is hydrogen, halogen, trifluoromethyl, an aliphatic hydrocarbon radical, hydroxy or is hydroxy which is etherified by an aliphatic, araliphatic or aromatic alcohol or by an aliphatic alcohol which is substituted by carboxy, by esterified carboxy or by amidated carboxy or which is esterified by an aliphatic or araliphatic carboxylic acid;

$R_3$ is hydrogen or an acyl radical which is derived from an organic carbonic acid, an organic carboxylic acid, a sulfonic acid, or a carbamic acid;

$X_1$ and $X_3$, independently of one another, are oxygen (—O—) or sulphur (—S—); and $X_2$ is a divalent aliphatic hydrocarbon radical which may be interrupted by an aromatic radical;

wherein the phenyl rings of formula I may be, independently of one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid;

wherein aryl in the above definitions may be, independently of one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid;

wherein a cycloaliphatic hydrocarbon radical may be substituted by an aliphatic radical.

2. A method according to claim 1, in which:

$R_1$ is amino which is mono- or disubstituted by a substituent selected from lower alkyl, lower alkenyl, lower alkynyl, phenyl-lower alkyl, phenyl-lower alkenyl, phenyl-lower alkynyl, phenyl, napthyl, indanyl, fluorenyl, cycloalkyl, and cycloalkenyl, cycloalkyl and cycloalkenyl each being unsubstituted or mono- or polysubstituted by lower alkyl, or is amino which is disubstituted by lower alkylene;

$R_2$ is hydrogen, halogen, trifluoromethyl, lower alkyl, lower alkenyl, lower alkynyl, hydroxy, lower alkoxy, lower alkenyloxy, phenyl-lower alkoxy, phenoxy, lower alkoxy substituted by carboxy, lower alkoxycarbonyl, aminocarbonyl or mono- or di-lower alkylaminocarbonyl, lower alkanoyloxy, lower alkenoyloxy or phenyl-lower alkanyloxy;

$R_3$ is hydrogen, alkoxycarbonyl or alkenyloxycarbonyl, each of which is unsubstituted or substituted by phenyl, naphthyl, indanyl or fluorenyl, or is cycloalkoxycarbonyl being unsubstituted or mono- or polysubstituted by lower alkyl, or is lower alkanoyl or phenyl-lower alkanoyl, or is benzoyl, naphthoyl, indanoyl or fluorenoyl, or is $C_1$–$C_7$-alkanesulfonyl, phenyl-$C_1$–$C_7$alkanesulfonyl, $C_3$–$C_7$-cycloalkanesulfonyl, or phenylsulfonyl, or is aminocarbonyl which is substituted by lower alkyl, phenyl-lower alkyl or phenyl;

$X_1$ and $X_3$, independently of one another, are O or S; and $X_2$ is lower alkylene, lower alkylene-phenylene-lower alkylene or lower alkylene-naphthylene-lower alkylene;

wherein the phenyl rings of formula I may be, independently of one another, substituted by one or more substituents selected from halogen, trifluoromethyl, lower alkyl, lower alkenyl, lower alkynyl, hydroxy, lower alkoxy, lower alkenyloxy, phenyl-lower alkoxy, lower alkanoyloxy, lower alkenoyloxy and phenyl-lower alkanoyloxy;

wherein the aromatic radicals in the above definitions may be, independently of one another, substituted by one or more substituents selected from halogen, trifluoromethyl, lower alkyl, lower alkenyl, lower alkynyl, hydroxy, lower alkoxy, lower alkenyloxy, phenyl-lower alkoxy, lower alkanoyloxy, lower alkenoyloxy and phenyl-lower alkanoyloxy.

3. A method according to claim 1, in which:

$R_1$ is amino which is mono- or disubstituted by a substituent selected from $C_1$–$C_7$-alkyl, phenyl-$C_1$–$C_7$-alkyl, phenyl and $C_3$–$C_6$-cycloalkyl, $C_3$–$C_6$-cycloalkyl being unsubstituted or mono- or polysubstituted by $C_1$–$C_7$alkyl, or is amino which is disubstituted by $C_3$–$C_6$-alkylene;

$R_2$ is hydrogen, hydroxy, $C_1$–$C_7$-alkoxy, $C_1$–$C_7$-alkoxy substituted by carboxy or lower alkoxycarbonyl or phenyl-$C_1$–$C_4$ alkoxy;

$R_3$ is hydrogen, $C_1$–$C_{12}$-alkoxy-carbonyl, $C_2$–$C_5$-alkanoyl, phenyl-$C_2$–$C_5$-alkanoyl, benzoyl which is unsubstituted or substituted by halogen, trifluoromethyl, $C_1$–$C_7$-alkyl, or $C_1$–$C_7$ alkoxy, $C_3$–$C_6$-cycloalkylcarbonyl which is unsubstituted or substituted by $C_1$–$C_7$-alkyl, or is benzoyl, naphthoyl, indanoyl or fluorenoyl, or is $C_1$–$C_7$alkanesulfonyl, phenyl-$C_1$–$C_7$alkanesulfonyl, $C_3$–$C_7$-cycloalkanesulfonyl, or phenylsulfonyl, or is aminocarbonyl which is substituted by $C_1$–$C_7$-alkyl, phenyl-$C_1$–$C_7$-alkyl or phenyl;

$X_1$ and $X_3$ each are —O—, or furthermore are, independently of one another, —O— or —S—; and $X_2$ is $C_2$–$C_7$-alkylene or $C_2$–$C_4$-alkylene-phenylene-$C_2$–$C_4$-alkylene;

wherein the phenyl rings of formula I may be unsubstituted or, furthermore, independently of one another, substituted by one or more substituents selected from halogen, trifluoromethyl, $C_1$–$C_7$-alkyl, and $C_1$–$C_7$-alkoxy;

wherein phenyl in the above definitions is unsubstituted or, furthermore, independently of one another, substituted by one or more substituents selected from halogen, trifluoromethyl, $C_1$–$C_7$-alkyl, and $C_1$–$C_7$-alkoxy.

4. A method according to claim 1, in which —CO—$R_1$ is located in position 4 (para) or 3 or 5 (meta) of the corresponding phenyl ring with respect to -$X_1$—; $R_2$— is located in position 2 (ortho) or 3 (meta) of the corresponding phenyl ring with respect to —$X_1$—; and —C(=NH)—NHR$_3$ is located in position 4 (para) of the corresponding phenyl ring with respect to —$X_3$—.

5. A method according to claim 1, in which the compound of formula I is of formula IA

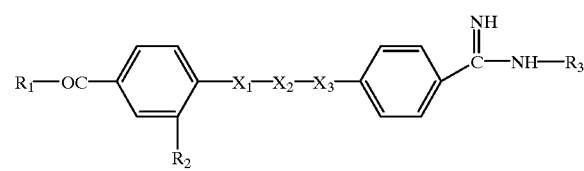

(IA)

wherein the C(=NH)—NHR$_3$ group may be in tautomeric or isomeric form, and in which:

$R_1$ is di-$C_1$–$C_4$-alkylamino, $C_1$–$C_4$alkyl-(phenyl)amino, $C_1$–$C_4$alkyl-(phenyl-$C_1$–$C_4$-alkyl)-amino, di-$C_3$–$C_6$-cycloalkylamino, which is unsubstituted or substituted by $C_1$–$C_4$-alkyl, or 1-piperidino substituted by $C_1$–$C_4$-alkyl;

$R_2$ is hydrogen, $C_1$–$C_4$-alkoxy or $C_1$–$C_4$-alkoxy which is substituted by carboxy, lower alkoxycarbonyl, aminocarbonyl or by mono- or di-lower alkylaminocarbonyl;

$R_3$ is hydrogen, $C_1$–$C_{12}$-alkoxycarbonyl, phenyl-$C_1$–$C_4$-alkoxycarbonyl, $C_2$–$C_5$-alkanoyl, benzoyl which is unsubstituted or substituted by halogen, trifluoromethyl, $C_1$–$C_4$-alkyl or by $C_1$–$C_4$-alkoxy, $C_3$–$C_6$-cycloalkylcarbonyl which is unsubstituted or substituted by $C_1$–$C_4$-alkyl;

$X_1$ and $X_3$ are —O—;

$X_2$ is $C_4$–$C_7$-alkylene;

wherein the phenyl rings of formula IA may be unsubstituted or, furthermore, independently of one another, substituted by one or more substituents selected from halogen, trifluoromethyl, $C_1$–$C_4$-alkyl, and $C_1$–$C_4$-alkoxy.

6. A method according to claim 5, in which:

$R_1$ is di-$C_1$–$C_4$-alkylamino, $C_1$–$C_4$-alkyl-(phenyl)-amino, $C_1$–$C_4$-alkyl-(phenyl-$C_1$–$C_4$-alkyl)-amino, di-$C_3$–$C_6$-cycloalkylamino, which is unsubstituted or substituted by $C_1$–$C_4$-alkyl, or 1-piperidino substituted by $C_1$–$C_4$-alkyl;

$R_2$ is hydrogen, $C_1$–$C_4$-alkoxy or $C_1$–$C_4$-alkoxy substituted by $C_1$–$C_4$-alkoxycarbonyl;

$R_3$ is hydrogen; or $R_3$ is lower alkanoyl;

$X_1$ and $X_3$ are —O—; and $X_2$ is $C_4$–$C_7$-alkylene.

7. A method according to claim 5, in which:

$R_1$ is di-$C_1$–$C_4$-alkylamino;

$R_2$ is hydrogen, $C_1$–$C_4$-alkoxy or $C_1$–$C_4$-alkoxy substituted by $C_1$–$C_4$-alkoxycarbonyl or by aminocarbonyl;

$R_3$ is $C_1$–$C_{12}$-alkoxycarbonyl, phenyl-$C_1$–$C_4$-alkoxycarbonyl, $C_2$–$C_5$-alkanoyl, benzoyl which is unsubstituted or substituted by halogen, trifluoromethyl, $C_1$–$C_4$-alkyl, or $C_1$–$C_4$-alkoxy, $C_3$–$C_6$-cycloalkylcarbonyl which is unsubstituted or substituted by $C_1$–$C_4$-alkyl;

$X_1$ and $X_3$ are —O—; and $X_2$ is $C_4$–$C_7$-alkylene.

8. A method according to claim 5, in which:

$R_1$ is di-$C_1$–$C_4$-alkylamino;

$R_2$ is hydrogen, $C_1$–$C_4$-alkoxy or $C_1$–$C_4$-alkoxy substituted by $C_1$–$C_4$-alkoxycarbonyl or by aminocarbonyl;

$R_3$ is hydrogen or $C_1$–$C_4$-alkanoyl;

$X_1$ and $X_3$ are —O—; and $X_2$ is $C_4$–$C_7$-alkylene.

9. A method according to claim 5, in which $R_1$ is di-isopropylamino, $R_2$ is methoxy, $R_3$ is hydrogen, $X_1$ and $X_3$ are —O— and $X_2$ is pentylene.

10. A method according to claim 1, in which the compound of formula I is of formula IB

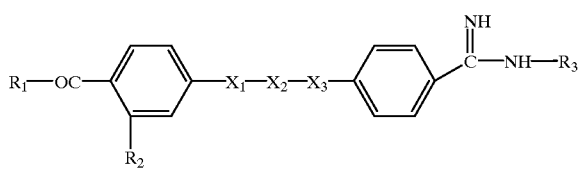

(IB)

wherein the C(=NH)—NHR$_3$ group may be in tautomeric or isomeric form, and in which:

$R_1$ is di-$C_1$–$C_4$-alkylamino, $C_1$–$C_4$alkyl-(phenyl)amino, $C_1$–$C_4$-alkyl-(phenyl-$C_1$–$C_4$-alkyl)-amino, di-$C_3$–$C_6$-cycloalkylamino, which is unsubstituted or substituted by $C_1$–$C_4$-alkyl, or 1-piperidino substituted by $C_1$–$C_4$-alkyl;

$R_2$ is hydroxy or $C_1$–$C_4$-alkoxy which is substituted by carboxy, lower alkoxycarbonyl, aminocarbonyl or by mono- or di-lower alkylaminocarbonyl;

$R_3$ is hydrogen, $C_1$–$C_{12}$-alkoxycarbonyl, phenyl-$C_1$–$C_4$-alkoxycarbonyl, $C_2$–$C_5$-alkanoyl, benzoyl which is unsubstituted or substituted by halogen, trifluoromethyl, $C_1$–$C_4$-alkyl, or $C_1$–$C_4$-alkoxy, $C_3$–$C_6$-cycloalkylcarbonyl which is unsubstituted or substituted by $C_1$–$C_4$-alkyl;

$X_1$ and $X_3$ are —O—; and $X_2$ is $C_4$–$C_7$-alkylene;

wherein the phenyl rings of formula IB may be unsubstituted or, furthermore, independently of one another, substituted by one or more substituents selected from halogen, trifluoromethyl, $C_1$–$C_4$-alkyl, and $C_1$–$C_4$-alkoxy.

11. A method according to claim 10, in which:

$R_1$ is di-$C_1$–$C_4$-alkylamino, $C_1$–$C_4$-alkyl-(phenyl)-amino, $C_1$–$C_4$alkyl-(phenyl-$C_1$–$C_4$-alkyl)-amino, di-$C_3$–$C_6$-cycloalkylamino, which is unsubstituted or substituted by $C_1$–$C_4$-alkyl, or 1-piperidino substituted by $C_1$–$C_4$-alkyl;

$R_2$ is hydroxy or $C_1$–$C_4$-alkoxy substituted by $C_1$–$C_4$-alkoxycarbonyl, or by aminocarbonyl;

$R_3$ is hydrogen; or $R_3$ is $C_2$–$C_5$-alkanoyl;

$X_1$ and $X_3$ are —O—; and $X_2$ is $C_4$–$C_7$-alkylene.

12. A method according to claim 10, in which:

$R_1$ is di-$C_1$–$C_4$-alkylamino;

$R_2$ is hydroxy or $C_1$–$C_4$-alkoxycarbonylmethoxy, or aminocarbonylmethoxy;

$R_3$ is hydrogen or $C_2$–$C_5$-alkanoyl;

$X_1$ and $X_3$ are —O—; and $X_2$ is $C_4$–$C_7$-alkylene.

13. A method according to claim 10, in which $R_1$ is di-isopropylamino, $R_2$ is hydroxy, $R_3$ is hydrogen, $X_1$ and $X_3$ are —O— and $X_2$ is pentylene.

14. A method according to claim 1, in which the compound of formula I or salt thereof is administered in combination with a pharmaceutically acceptable carrier.

15. A method according to claim 1, in which the disease is chronic bronchitis.

16. A method according to claim 9, in which the compound of formula I or salt thereof is administered in combination with a pharmaceutically acceptable carrier.

17. A method according to claim 9, in which the disease is chronic bronchitis.

18. A method according to claim 13, in which the compound of formula I or salt thereof is administered in combination with a pharmaceutically acceptable carrier.

19. A method according to claim 13, in which the disease is chronic bronchitis.

20. A medicament suitable for pulmonary administration comprising a compound of formula I as specified in claim 1, or a pharmaceutically acceptable salt thereof, or a mixture of said compound or salt with a pharmaceutically acceptable carrier therefor, the compound, salt or mixture being in inhalable form.

21. A medicament suitable for pulmonary administration comprising a compound of formula IA as specified in claim 5, or a pharmaceutically acceptable salt thereof, or a mixture of said compound or salt with a pharmaceutically acceptable carrier therefor, the compound, salt or mixture being in inhalable form.

* * * * *